United States Patent [19]

Ishihara et al.

[11] Patent Number: 5,325,859
[45] Date of Patent: Jul. 5, 1994

[54] ULTRASONIC DIAGNOSIS APPARATUS

[75] Inventors: Ken Ishihara, 1-15 Chigusa-1-chome, Takarazuka-shi; Toshihiko Kawano, Nagareyama, both of Japan

[73] Assignees: Ken Ishihara, Takarazuka; Hitachi Medical Corp., Tokyo, both of Japan

[21] Appl. No.: 3,623

[22] Filed: Jan. 13, 1993

[30] Foreign Application Priority Data

Jan. 14, 1992 [JP] Japan .................. 4-023434

[51] Int. Cl.⁵ .............................. A61B 8/00
[52] U.S. Cl. .............................. 128/660.07
[58] Field of Search ............. 128/660.04, 660.05, 128/660.07; 73/625, 626

[56] References Cited

U.S. PATENT DOCUMENTS

| 4,583,552 | 4/1986 | Iinuma | 128/660.05 |
| 5,016,642 | 5/1991 | Dukes et al. | 128/660.07 |
| 5,090,413 | 2/1992 | Yoshioka | 128/660.07 |
| 5,099,847 | 3/1992 | Powers et al. | 128/660.07 |

OTHER PUBLICATIONS

"Study of Image Memory System for High Frame Rate Ultrasound Equipment", T. Kawahara et al. Collection of Lectures The Japan Society of Ultrasonics in Medicine, Oct.-Nov. 1990, pp. 601-602.

Primary Examiner—William E. Kamm
Assistant Examiner—George Manuel
Attorney, Agent, or Firm—Antonelli, Terry, Stout & Kraus

[57] ABSTRACT

An ultrasonic diagnosis apparatus comprises an ultrasonic wave transmitting/receiving unit for transmitting ultrasonic signals to a subject and receiving reflected echo signals reflected from the subject; a unit for controlling the ultrasonic wave transmitting/receiving unit such that the ultrasonic signals repetitively scan the subject at a predetermined scan period; an image memory unit for storing a plurality of image data pieces; a detection unit for detecting biophysical signals of the subject; a unit for setting a reference timing on the basis of the biophysical signals; an image display unit for displaying an image corresponding to the image data piece being delivered out of the image memory unit, the image display unit displaying the image at a predetermined display unit; a unit for controlling the image memory unit so as to store the plurality of image data pieces based on the reflected echo signals, wherein the plurality of image data pieces respectively correspond to two-dimensional images of the subject at different time points and the time points associated with the plurality of image data pieces are sequentially displaced by a first time interval and in synchronism with the reference timing; and a control unit for controlling the memory unit so as to sequentially deliver the plurality of image data pieces stored in the image memory unit at second time intervals longer than the first time interval during scanning of the ultrasonic signals.

14 Claims, 10 Drawing Sheets

ULTRASONIC DIAGNOSIS APPARATUS

BACKGROUND OF THE INVENTION

The present invention relates to an ultrasonic diagnosis apparatus for producing two-dimensional images of a region of interest of a subject by utilizing ultrasonic waves.

A conventional ultrasonic diagnosis apparatus comprises an ultrasonic wave transmitting/receiving unit for transmitting and receiving ultrasonic waves to and from a subject, a two-dimensional scan unit for repetitively producing data of two-dimensional images inside a subject inclusive of a moving tissue at a predetermined period by using reflected echo signals from the ultrasonic wave transmitting/receiving unit, an image memory unit for storing time-sharing images produced from the two-dimensional scan unit, and an image display unit for displaying image data delivered out of the image memory unit. Particularly, in a diagnostic ultrasound equipment for cardiac study, electrocardiographic electrodes are attached to hands and legs of a subject to detect biophysical signals and obtain an electrocardiogram (ECG) and the thus obtained ECG is utilized through ECG synchronous method to display a still image of a region of interest at a desired timing. Also, in a recent ultrasonic diagnosis apparatus, an image memory of large capacity is used as an image memory unit and image data pieces of a moving region collected during real time (during transmission and reception of ultrasonic waves) are stored in the image memory and after being frozen or after completion of the transmission and reception of ultrasonic waves, are readout of the image memory of large capacity sequentially so as to be reproduced and displayed in slow motion fashion ("Study of Image Memory System for High Frame Rate Ultrasound Equipment" by K. Kawano et al, Collection of Lectures of the Japan Society of Ultrasonics in Medicine, Oct. to Nov. 1990, pp. 601–602).

SUMMARY OF THE INVENTION

However, the above conventional ultrasonic diagnosis apparatus are disadvantageous in the following points. More particularly, in display in the former apparatus based on the ECG synchronous method, only one still image can be obtained in a cardiac cycle during real time and so motion of a moving region cannot be recognized. In slow motion display in the latter apparatus using the large-capacity image memory, images are reproduced and displayed after being frozen and so motion of a moving region such as the heart cannot be observed in slow motion fashion during real time. Thus, neither of the conventional ultrasonic diagnosis apparatus can provide slow motion display of motion of a moving region inside a subject during real time and so can permit observation of details of behavior of the moving blood vessel or heart to provide sufficient diagnosis information during real time.

Accordingly, an object of the present invention is to provide an ultrasonic diagnosis apparatus which can permit slow motion display of motion of a moving region in a subject during real time.

To accomplish the above object, according to one aspect of the invention, an ultrasonic diagnosis apparatus comprises an ultrasonic wave transmitting/receiving unit for transmitting ultrasonic signals to a subject and receiving reflected echo signals reflected from the subject; a unit for controlling the ultrasonic wave transmitting/receiving unit such that the ultrasonic signals repetitively scan the subject at a predetermined scan period; an image memory unit for storing a plurality of image data pieces; a detection unit for detecting biophysical signals of the subject; a unit for setting a reference timing on the basis of the biophysical signals; an image display unit for displaying an image corresponding to the image data piece being delivered out of the image memory unit, the image display unit displaying the image at a predetermined display period; a unit for controlling the image memory unit so as to store the plurality of image data pieces based on the reflected echo signals, wherein the plurality of image data pieces respectively correspond to two-dimensional images of the subject at different time points and the time points associated with the plurality of image data pieces are sequentially displaced by a first time interval and in synchronism with the reference timing; and a control unit for controlling the memory unit so as to sequentially deliver the plurality of image data pieces stored in the image memory unit at second time intervals longer than the first time interval during scanning of the ultrasonic signals.

According to this ultrasonic diagnosis apparatus, motion of a moving region such as the blood vessel or heart can be displayed in slow motion fashion during real time (during transmission and reception of the ultrasonic signals) and therefore diagnosis information which has hitherto been liable to be missed can be obtained sufficiently.

The first time interval may be N (N being an integer which is one or more) times the scan period. The second time interval may be K (K being an integer which is one or more) times the display period. The second time interval may be M (M being an integer which is two or more) times the first time interval.

The ultrasonic diagnosis apparatus may further comprise a unit for setting the second time interval externally.

The control unit may include a selector unit for selecting one of the second time interval which is M (M being an integer which is two or more) times the first time interval and the second time interval which is K (K being an integer which is one or more) times the display period. In this case, the first time interval may be L (L being an integer which is one or more) times the scan period.

According to another aspect of the invention, an ultrasonic diagnosis apparatus comprises an ultrasonic wave transmitting/receiving unit for transmitting ultrasonic signals to a subject and receiving reflected echo signals reflected from the subject; a unit for controlling the ultrasonic wave transmitting/receiving unit such that the ultrasonic signals repetitively scan the subject at a predetermined scan period; a first image memory unit for storing a plurality of image data pieces; a second image memory unit for storing a single image data piece; a detection unit for detecting biophysical signals of the subject; a unit for setting a reference timing on the basis of the biophysical signals; an image display unit for displaying an image corresponding to an image data piece being inputted to the image display unit, the image display unit displaying the image at a predetermined display period; a unit for controlling the first image memory unit so as to store the plurality of image data pieces based on the reflected echo signals, wherein the plurality of image data pieces respectively correspond to two-dimensional images of the subject at different time points and the time points associated with the plurality of image data pieces are sequentially displaced by a first time interval and in synchronism with the reference timing; a unit for sequentially overwriting respective image data pieces based on the reflected echo signals in the second memory unit at third time intervals during scanning of the ultrasonic wave signals; a first control unit for controlling the first image memory so as to sequentially deliver the plurality of image data pieces stored in the first image memory unit at second time intervals longer than the first time interval during scanning of the ultrasonic signals; a second control unit for controlling the second memory unit so as to sequentially deliver the image data pieces stored in the second image memory unit; and a display control unit for displaying on the image display unit both of an image corresponding to the image data piece being delivered out of the first memory unit and an image corresponding to the image data piece being delivered out of the second memory unit, on the basis of the image data piece being delivered out of the first memory unit and the image data piece being delivered out of the second memory unit.

According to this ultrasonic diagnosis apparatus, motion of a moving region such as the blood vessel or heart can be displayed in slow motion fashion during real time (during transmission and reception of the ultrasonic signals) and therefore diagnosis information which has hitherto been liable to be missed can be obtained sufficiently. In addition, according to this ultrasonic diagnosis apparatus, a so-called real-time original image can be observed concurrently with observation of a slow motion image, thereby providing more detailed diagnosis information about a region of interest.

The first time interval may be N (N being an integer which is one or more) times the scan period. The second time interval may be K (K being an integer which is one or more) times the display period. The second time interval may be M (M being an integer which is two or more) the first time interval. The third time interval may be P (P being an integer which is one or more) times the scan period.

The ultrasonic diagnosis apparatus may further comprise a unit for setting the second time interval externally.

The display control unit may include a first line memory unit for sequentially storing respective partial data, corresponding to one horizontal scanning, included in the image data piece being delivered out of the first image memory unit; a second line memory unit for sequentially overwriting respective partial data, corresponding to one horizontal scanning, included in the image data piece being delivered out of the second image memory unit; and a unit for alternately supplying to the image display unit data, corresponding in amount to ½ horizontal scanning, included in the partial data stored in the first line memory unit and data, corresponding in amount to ½ horizontal scanning, included in the partial data stored in the second line memory unit. In this case, both of the slow motion image and real-time image can be displayed simultaneously without reducing them in scale.

DESCRIPTION OF THE PREFERRED EMBODIMENTS

Ultrasonic diagnosis apparatuses according to the invention will now be described in detail with reference to the accompanying drawings.

Figure 1:
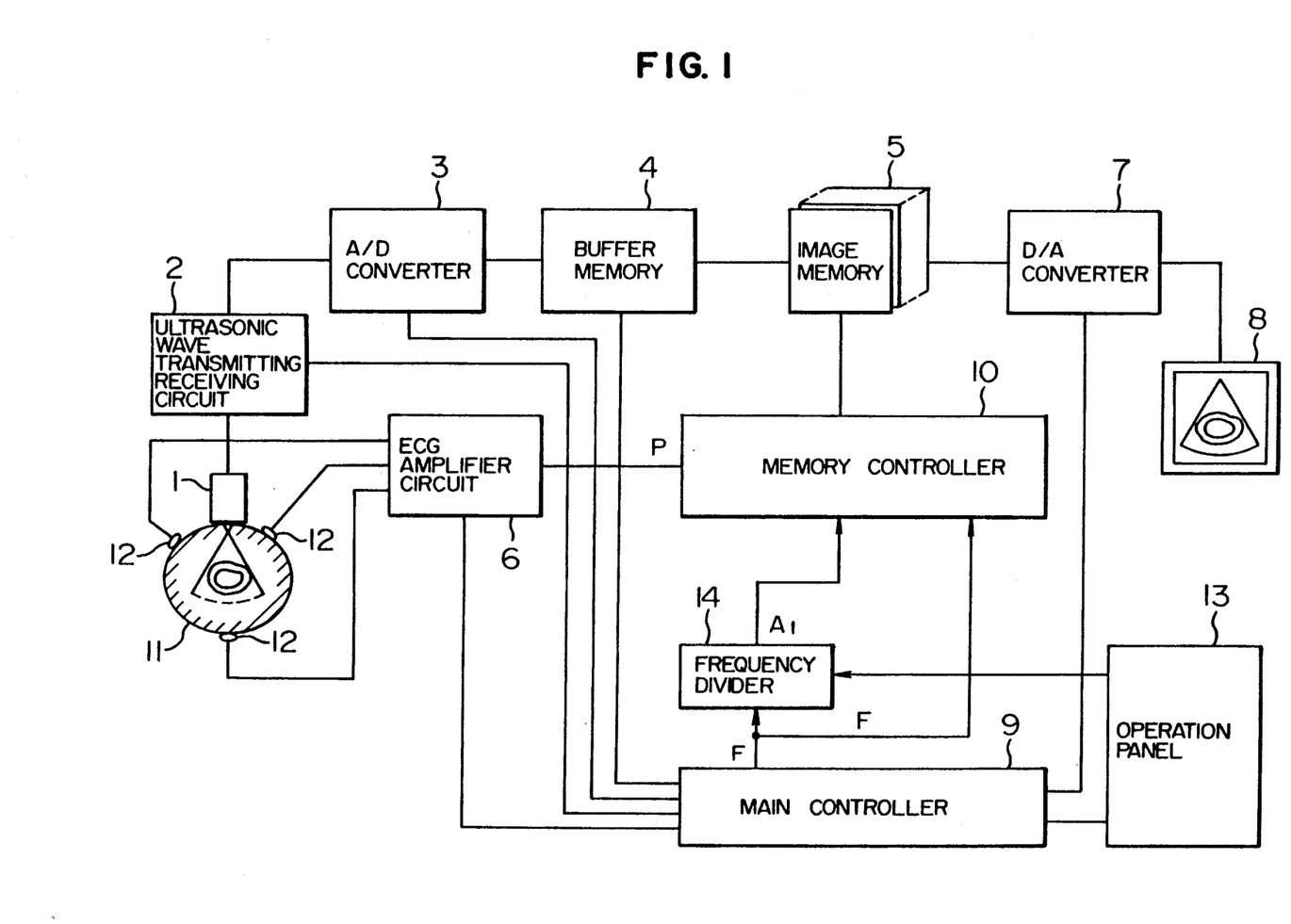
FIG. 1 is a block diagram showing an ultrasonic diagnosis apparatus according to an embodiment of the invention.

FIG. 1 is a block diagram showing an ultrasonic diagnosis apparatus according to an embodiment of the invention. The ultrasonic diagnosis apparatus is for obtaining two-dimensional images of a region of interest of a subject by utilizing ultrasonic waves and it comprises as shown in FIG. 1 a probe 1, an ultrasonic wave transmitting/receiving circuit 2, an A/D converter 3, a buffer memory 4, an image memory 5, an ECG amplifier circuit 6, a D/A converter 7, an image display 8 and a main controller 9 and a memory controller 10 as well.

The probe 1 is adapted to transmit ultrasonic signals to a subject 11 by performing beam scanning mechanically or electronically and receive reflected echo signals reflected from the subject 11, and it incorporates a plurality of oscillators not shown which serve as generation sources of ultrasonic waves and act to receive reflected echoes. The ultrasonic wave transmitting/receiving circuit 2 is for transmitting timing pulses to the probe 1 to cause it to generate ultrasonic waves and for processing received reflected echo signals and it incorporates, though not illustrated, known transmitting pulser and transmitting delay circuits for forming ultrasonic beams transmitted from probe 1 to subject 11, receiving amplifiers for amplifying reflected echo signals received by the oscillators of the probe 1, and a beam-forming circuit comprised of a receiving delay circuit and adder for forming a receiving ultrasonic beam by putting the received reflected echo signals in phase and adding them together. The ultrasonic wave transmitting/receiving circuit 2 also incorporates a reflected echo signal processing circuit having a gain control circuit for controlling a display sensitivity, a dynamic range control circuit for performing a contrast adjustment, and a detection circuit for performing a process including an enhancement process and an envelope detection with respect to a reflected echo signal. The ultrasonic wave transmitting/receiving circuit 2 responds to a control signal from the main controller to control the probe 1 so as to cause it to scan the ultrasonic beams in a predetermined direction inside a body of the subject 11 and the scanning is repeated at a predetermined scan period to produce a plurality of two-dimensional images.

The A/D converter 3 receives the reflected echo signals from the ultrasonic wave transmitting/receiving circuit 2 and converts them into digital signals. The buffer memory 4 incorporates two line memories and is operative to repeat alternate write and read of digital signals delivered out of the A/D converter 3 to and from the two line memories every scanning line or every plural scanning lines of ultrasonic beams in order to transmit the digital signals to the image memory 5 to be described later. A plurality of data pieces indicative of two-dimensional images in the subject including moving regions can be obtained at an ultrasonic wave transmitting period (scan period) on the basis of the reflected echo signals delivered out of the ultrasonic wave transmitting/receiving circuit 2 and the plurality of two-dimensional image data pieces are stored in the image memory in response to a control signal from the memory controller 10.

The image memory 5 serves as an image storing unit which sequentially stores a plurality of time-sharing images delivered out of the buffer memory 4 and consists of, for example, a semiconductor memory having a storage capacity enough to store images of plural frames (for example, 8 frames).

The ECG amplifier circuit 6 serves as a timing setting unit which sets a predetermined reference timing for image formation on the basis of biophysical signals which are detected by electrodes 12 and representative of, for example, a heartbeat of the subject 11 and it incorporates, though not shown in the figure, an isolation amplifier for insulating and amplifying ECG signals produced from the electrodes 12 attached to, for example, hands and legs of the subject 11, an R-wave timing detection circuit for detecting an R-wave timing, serving as a reference, from the thus obtained ECG signal waveforms, and an R-wave delay pulse generator responsive to a signal inputted by the operator from an operation panel 13 to generate a timing pulse which permits setting of a reference timing delayed by an optional delay time desired by the operator relative to the reference R-wave timing. In the present invention, the biophysical signal is in no way limited to the ECG signal.

The D/A converter 7 is operative to convert the image data delivered out of the image memory 5 into analog video signals. The image display 8 is adapted to receive the analog video signals from the D/A converter 7 to display an image in television display fashion and for example, it is a television monitor.

The main controller 9 is adapted to control operation of the individual components and for example, it is a central processing unit (CPU).

In the present embodiment, the memory controller 10 is particularly connected between the ECG amplifier circuit 6 and image memory 5. The memory controller 10 is operative to store a plurality of image data pieces in the image memory 5 in synchronism with the reference timing fed from the ECG amplifier circuit 6 and also sequentially reads image data pieces in synchronism with, for example, a display period of the image display 8 at a rate of one out of n (n being positive integer) periods in order to control slow motion display. More particularly, the memory controller 10 performs controlling slow motion display of image data of plural frames from the R-wave delay pulse generator on a real time basis by writing image data of plural frames delivered out of the buffer memory 4 into the image memory 5 in synchronism with the reference standing for the R-wave delay pulse delivered out of the ECG amplifier circuit 6 and reading the thus written image data pieces sequentially at a longer time interval than the reference for writing.

The operation of the ultrasonic diagnosis apparatus shown in FIG. 1 and having the above construction will now be described with reference to FIGS. 2A to 2E and FIGS. 3 and 4.

Firstly, the probe 1 shown in FIG. 1 is applied or put on a position corresponding to a region of interest of the subject 11 and ultrasonic waves are transmitted to the region of interest. At that time, each ultrasonic wave transmitted from the probe 1 is shaped by the transmitting delay circuit inside the ultrasonic wave transmitting/receiving circuit 2 so that it may take the form of a thin beam at the region of interest. The transmitting beams impinging upon the region of interest are reflected thereby to provide reflected echoes which in turn are received by the probe 1 and fetched through the receiving delay circuit and adder inside the ultrasonic wave transmitting/receiving circuit 2 so as to be formed into received beams. Transmission/reception of ultrasonic waves from the probe 1 is repeated at a predetermined period in sequentially changing directions of ultrasonic wave transmission/reception to permit the scanning of the region of interest. A series of scannings are carried out in response to a signal corresponding to each frame start signal F (FIG. 2B) applied from the main controller 9 to the ultrasonic wave transmitting/receiving circuit 2.

The reflected echo signals delivered out of the ultrasonic wave transmitting/receiving circuit 2 are inputted to the A/D converter 3 so as to be converted into digital signals which in turn are transmitted to the buffer memory 4. The buffer memory 4 has a plurality of line memories, write and read of which are controllably switched by the main controller 9 each time that the ultrasonic wave transmitting/receiving directions change, thus ensuring that digital echo signals can be transmitted to the image memory 5 each time that the individual received beams are sequentially inputted. The image memory 5 can store two-dimensional image data pieces corresponding to, for example, 8 frames.

When the ultrasonic wave scanning for one frame image is completed under the control of the ultrasonic wave transmitting/receiving circuit 2, the probe 1 returns the scanning direction to the initial state to repeat transmission/reception of ultrasonic waves and performs the scanning by changing the transmitting/ receiving directions sequentially. In other words, the series of scannings (ultrasonic wave scannings for one frame image) are repeated at the predetermined scan period (the period of frame start signal F). Accordingly, two-dimensional image data pieces corresponding to one frame are sequentially transmitted to the image memory 5 at a rate of the period of the frame start signal F. Individual two-dimensional image data pieces correspond to two-dimensional images of the subject 11 at different time points and the adjacent time points with which the individual two-dimensional image data pieces are associated are displaced from each other by the period of the frame start signal F.

Figure 2A:
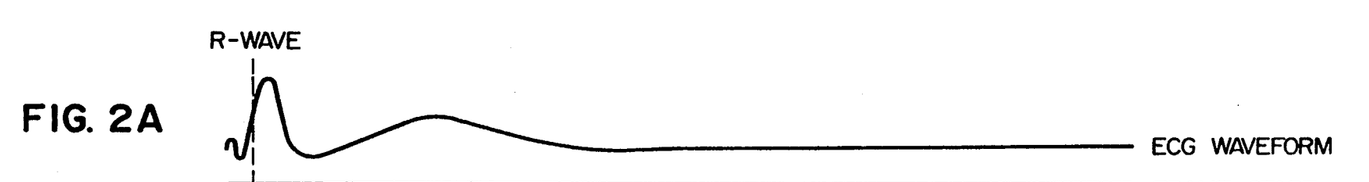
FIGS. 2A to 2E are timing charts showing the operation of the ultrasonic diagnosis apparatus shown in FIG. 1.
Figures 2B, 2C:
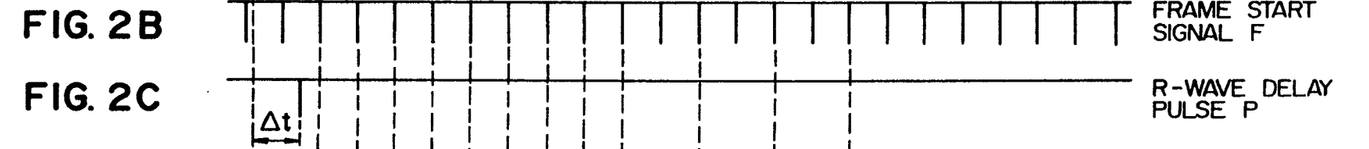

On the other hand, a frequency divider circuit 14 shown in FIG. 1 prepares a frequency division signal A1 by dividing the frequency of the frame start signal F in accordance with a frequency division ratio (for example, ½) determined by a control signal from the operation panel 13 shown in FIG. 1 and transmits the frequency division signal A1 to the memory controller 10. By manipulating the operation panel 13, the frequency division ratio can be set to different values. The memory controller 10 is also supplied with the frame start signal F from the main controller 9. The ECG amplifier circuit 6 shown in FIG. 1 detects, in addition to ECG waveforms of the subject 11, an R-wave timing serving as reference as shown in FIG. 2A, and an R-wave delay pulse P delayed by a desired delay time $\Delta t$ set through the operation panel 13 relative to the R-wave timing is delivered out of the circuit 6 as shown in FIG. 2C and supplied to the memory controller 10.

Figure 3:
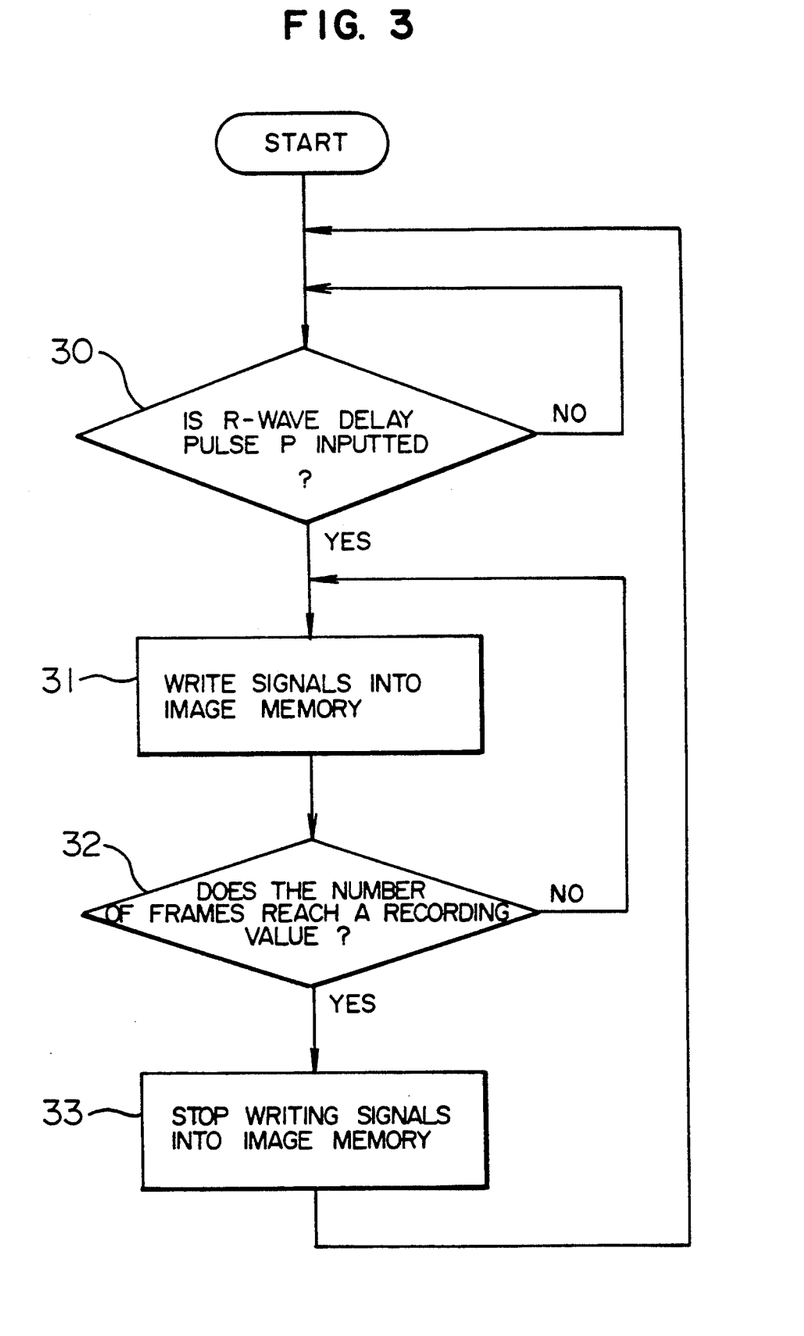
FIG. 3 is a flow chart showing an operation of the ultrasonic diagnosis apparatus shown in FIG. 1.
Figure 4:
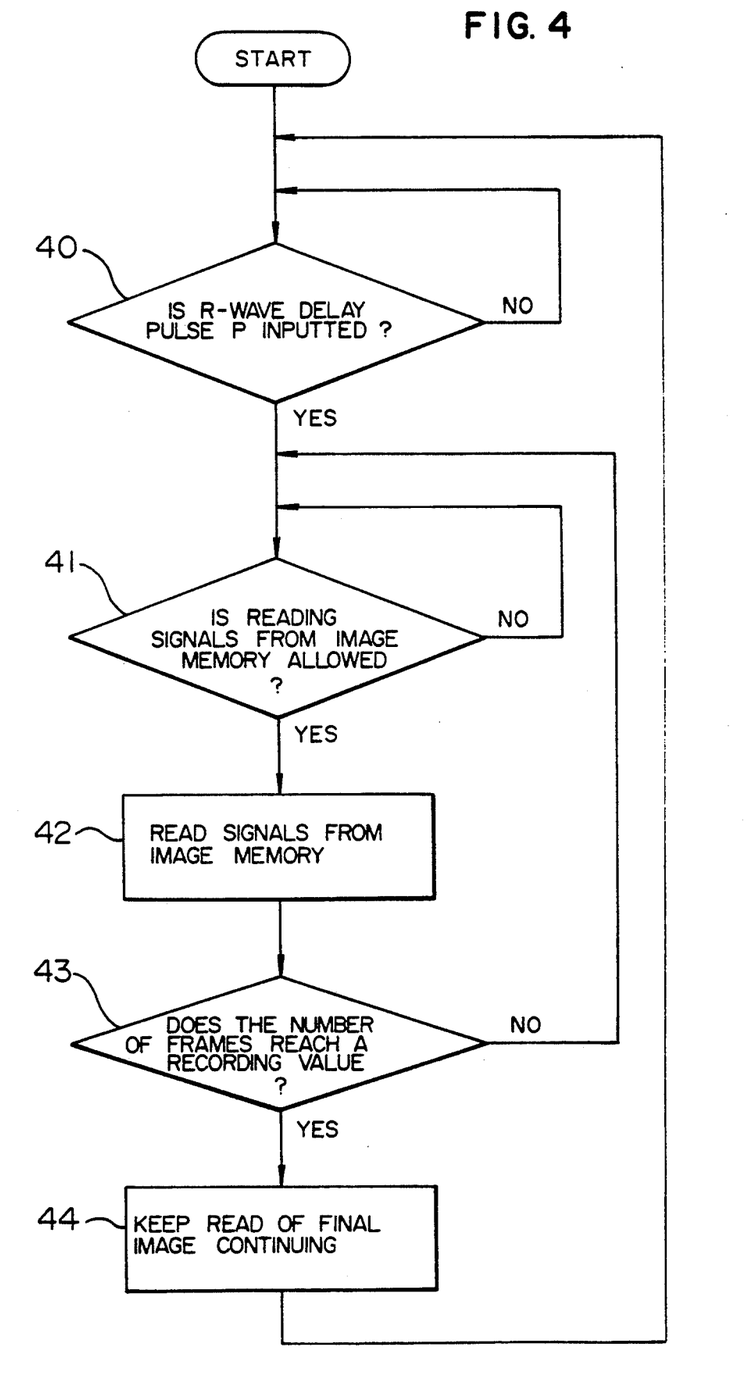
FIG. 4 is a flow chart showing another operation of the ultrasonic diagnosis apparatus shown in FIG. 1.

Then, the memory controller 10 controls write of data into the image memory 5 as shown in FIG. 3 and read of data from the image memory 5 as shown in FIG. 4 to accomplish slow motion display of a moving region during real time (during transmission/reception of the ultrasonic waves).

Figure 2D:
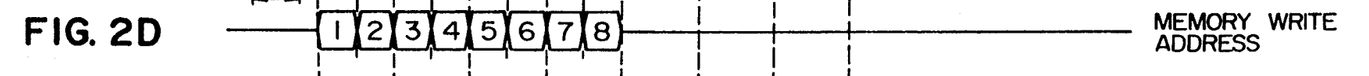

Controlling write of data into the image memory 5 will first be described with reference to FIG. 3. In step 30, it is decided whether or not an R-wave delay pulse P is inputted to the memory controller 10. If the R-wave delay pulse is not inputted, the program waits until it is inputted but if inputted, the program proceeds to step 31. In step 31, write signals and write address signals are supplied to the image memory 5 so that two-dimensional image data pieces for one frame transmitted from buffer memory 4 to image memory 5 may be stored in the image memory 5 in synchronism with the frame start signal F. Subsequently, it is decided in step 32 whether the number of frames of two-dimensional image data pieces stored in the image memory 5 reaches a predetermined recording value (for example, 8). If the predetermined recording value is not reached, the program returns to step 31 and repeats steps 31 and 32. If reached, the program proceeds from step 32 to step 33. As shown in FIG. 2D, write addresses of two-dimensional image data for one frame used in step 31 sequentially change each time step 31 repeats itself. It will be appreciated that write address numbers shown in FIG. 2D each represent an address of the entirety of two-dimensional image data pieces for one frame and obviously addresses of individual pixels contained in one frame data are different from each other. In step 33, write of two-dimensional image data into the image memory 5 is stopped and thereafter the program returns to step 30.

Figure 2E:
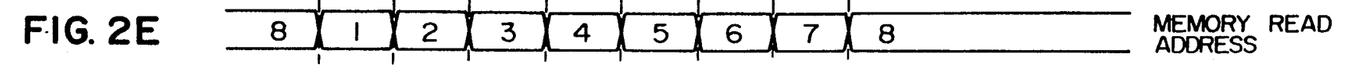

Controlling read of data from the image memory 5 will now be described with reference to FIG. 4. The data read control is carried out in parallel with the data write control shown in FIG. 3. In step 40, it is decided whether or not an R-wave delay pulse P is inputted to the memory controller 10. If the R-wave delay pulse is not inputted, the program waits until it is inputted but if inputted, the program proceeds to step 41. In step 41, it is decided whether two-dimensional image data pieces for corresponding one frame which have been stored in accordance with step 31 of FIG. 3 are allowable for reading. If not allowable, the program waits until they become allowable for reading and if allowable, the program proceeds to step 42. It is to be noted that read of two-dimensional image data may be allowed to start before write of entirety of two-dimensional image data for corresponding one frame is completed. In step 42, read signals and read address signals are supplied to the image memory 5 so that two-dimensional image data pieces for one frame may be read out of the image memory 5 in synchronism with the aforementioned frequency division signal resulting from ½ frequency division of the frame start signal F. Subsequently, it is decided in step 43 whether the number of frames of two-dimensional image data read out of the image memory 5 reaches a predetermined recording value (for example, 8). If the predetermined recording value is not reached, the program returns to step 41 and repeats steps 41 to 43. If reached, the program proceeds from step 43 to step 44. As shown in FIG. 2E, read addresses of two-dimensional image data for one frame used in step 42 sequentially change each time that step 42 repeats itself and the order of the read addresses coincides with that of the write addresses. It will be appreciated that read address numbers shown in FIG. 2E each represent an address of the entirety of two-dimensional image data pieces for one frame and obviously addresses of individual pixels contained in one frame data are different from each other. In step 44, read of two-dimensional image data finally read out of the image memory is caused to keep continuing and thereafter the program returns to step 40. Two-dimensional image data read out of the image memory 5 is converted by the D/A converter 7 into analog video signals and images corresponding to the two-dimensional image data pieces are displayed on the image display 8. Under the control of the main controller 9, images are displayed on the image display 8 at a predetermined display period.

FIG. 2E shows an example wherein the frame start signal F is delivered at a rate of one out of two during read but when the number of image frames allowed to be stored in the image memory 5 is supposed to be M and n is supposed to be positive integer, n can be set optionally within a range in which $n \times M \times T_f$ does not exceed one cardiac cycle, where $T_f$ is a scan period for obtaining one image. When read of the final image, for example, of the 8-th frame image is completed, display of the final image may be caused to keep continuing until the next R-wave delay pulse P is detected.

Figure 12A:
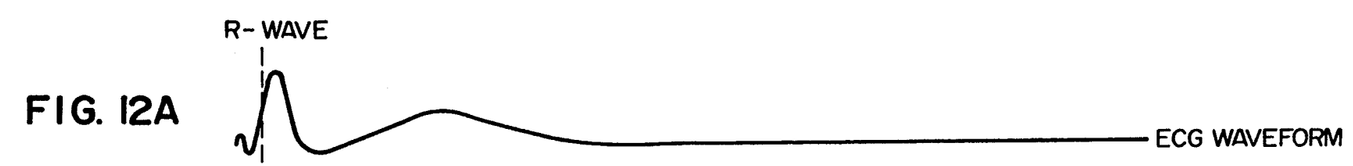
FIGS. 12A to 12E are timing charts showing an operation of an ultrasonic diagnosis apparatus.
Figures 12B, 12C, 12D:
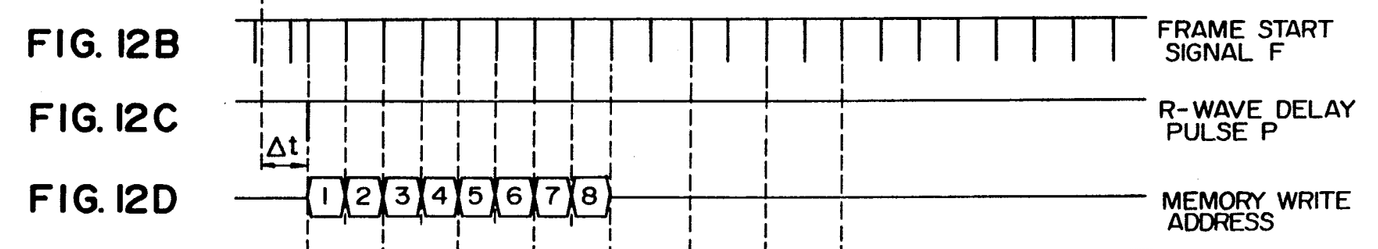
Figure 12E:
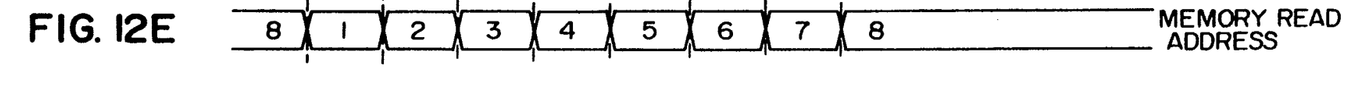

In the case shown in FIGS. 2A to 2E, the timing of the frame start signal F may not coincide with the timing of R-wave delay pulse P. However, as shown in FIGS. 12A to 12B, the frame start signal F may be forced to coincide with the timing of R-wave delay pulse P so that the scan is forced to return to the scan start state in response to the R-wave delay pulse even if the scan for one image is not completed. In this case, slow motion images obtained after an arbitrary cardiac timing can be displayed regardless of the start timing of the scan period.

As will be seen from the operation described above, according to the ultrasonic diagnosis apparatus shown in FIG. 1, images corresponding to two-dimensional image data pieces of individual frames can be displayed during transmission/reception of ultrasonic waves at a time interval which is, for example, twice the interval between adjacent time points associated with adjacent frames of two-dimensional image data pieces. Accordingly, motion of a moving region such as a blood vessel or the heart can be displayed in slow motion fashion during real time, thereby ensuring that diagnosis information which has hitherto been liable to be missed can be obtained sufficiently.

While in the embodiment of FIG. 1 described so far the write period of two-dimensional image data coincides with the period of frame start signal F, the former period may be twice or more the latter period. The read period of two-dimensional image data may be coincident or may not be coincident with the display period of the image display 8 or it may be one or more integer times the display period. Further, the read period of two-dimensional image data may be or may not be two or more times the write period of two-dimensional image data.

In the embodiment shown in FIG. 1, a so-called original image on real time can be displayed in place of the aforementioned slow motion display by manipulating the operation panel 13 to set the frequency division ratio of the frequency divider circuit 14 to 1 (one).

An ultrasonic diagnosis apparatus according to another embodiment of the invention will now be described with reference to FIG. 5.

Figure 5:
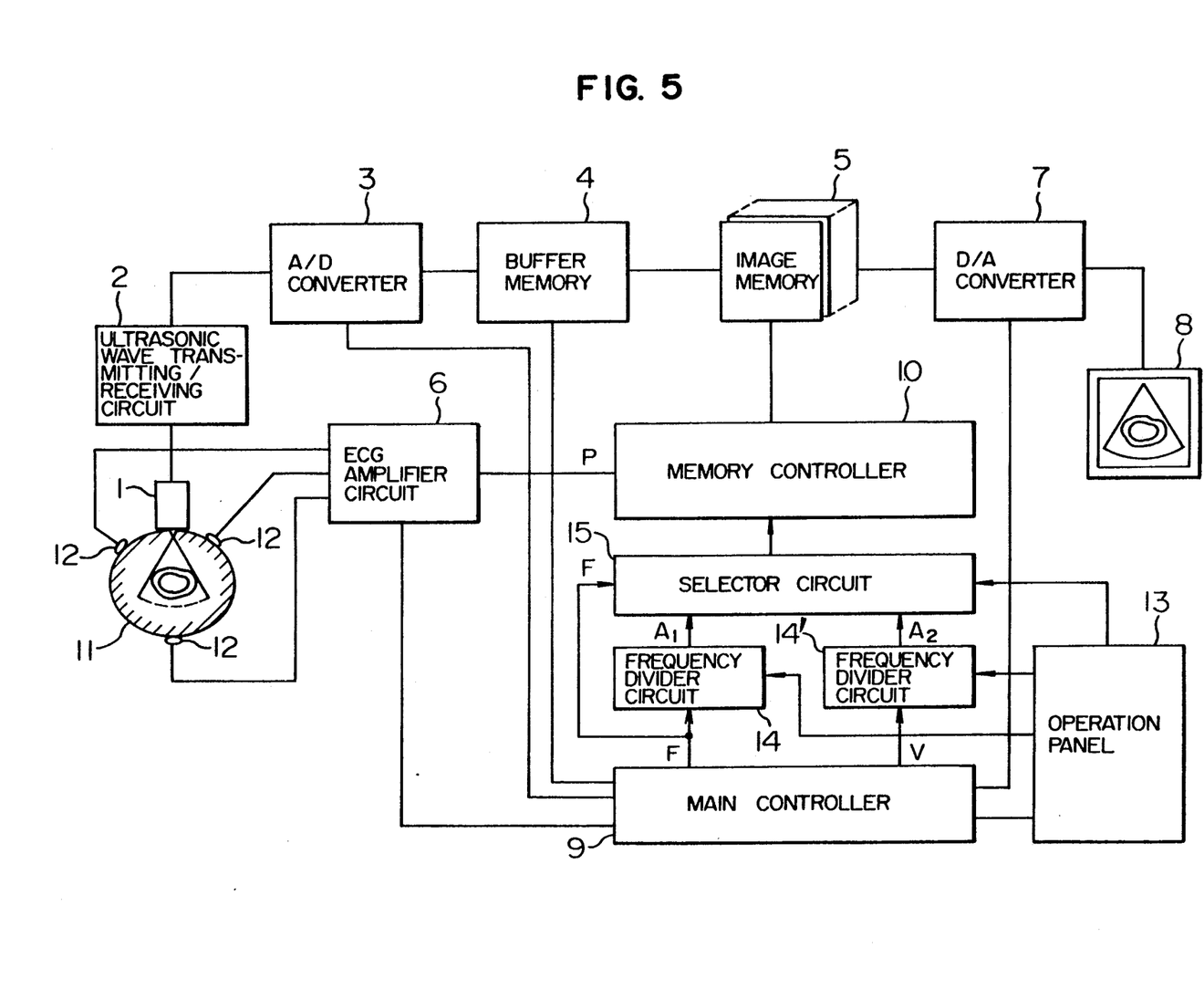
FIG. 5 is a block diagram showing an ultrasonic diagnosis apparatus according to another embodiment of the invention.

FIG. 5 is a block diagram showing the present embodiment. In this embodiment, a selector circuit 15 for selecting either sequential delivery of image data from the image memory 5 in synchronism with the transmitting/receiving period of the ultrasonic wave transmitting/receiving circuit 2 or sequential delivery of image data in synchronism with the display period of the image display 8. More specifically, the main controller 9 is associated with a second frequency divider circuit 14' in addition to the aforementioned frequency divider circuit 14, the frequency of a television vertical synchronizing signal (see FIG. 6E) delivered out of the main controller 9 is suitably divided at a frequency division ratio (which may be one) of the second frequency divider circuit 14' to provide a second frequency division signal A2 (see FIG. 6F), the second frequency division signal A2 and a first frequency division signal A1 prepared by the first frequency divider circuit 14 are inputted to the selector circuit 15 so that it may select one of the signals A1 and A2, and the selected frequency division signal is transmitted to the memory controller 10.

Figure 6A:
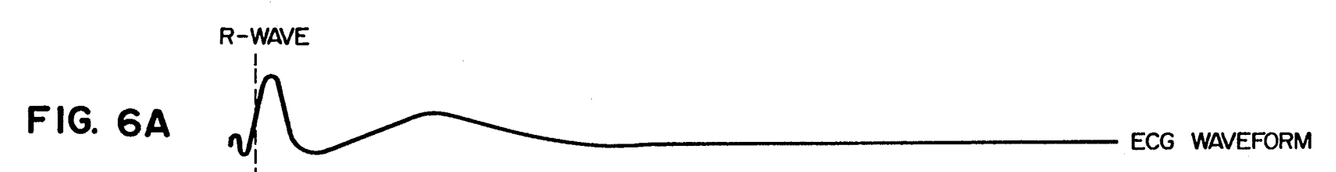
FIGS. 6A to 6F are timing charts showing the operation of the ultrasonic diagnosis apparatus shown in FIG. 5.
Figure 6B:
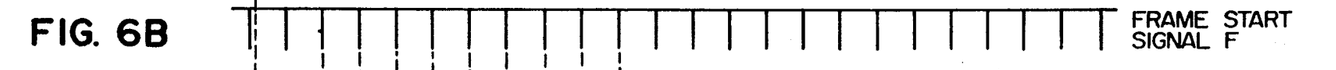
Figure 6C:
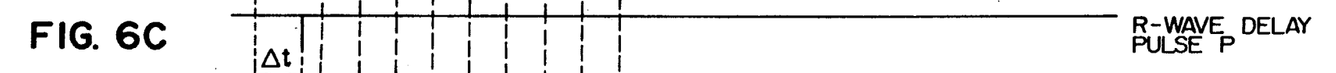
Figure 6D:
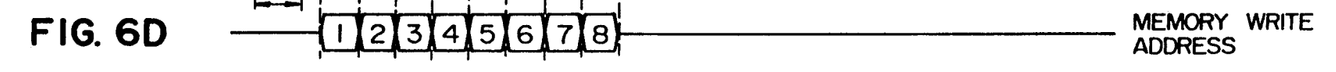
Figure 6E:
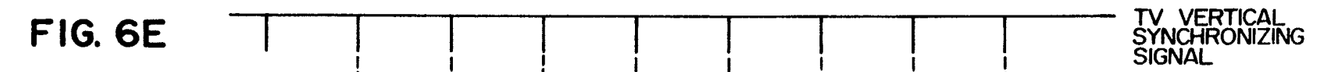
Figure 6F:
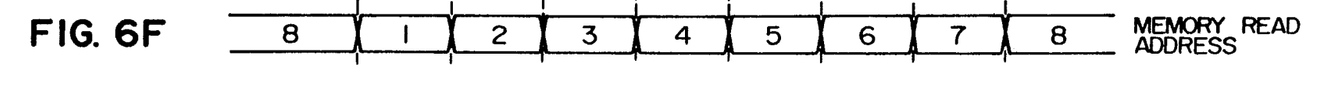
Figures 7A, 7B, 7C:
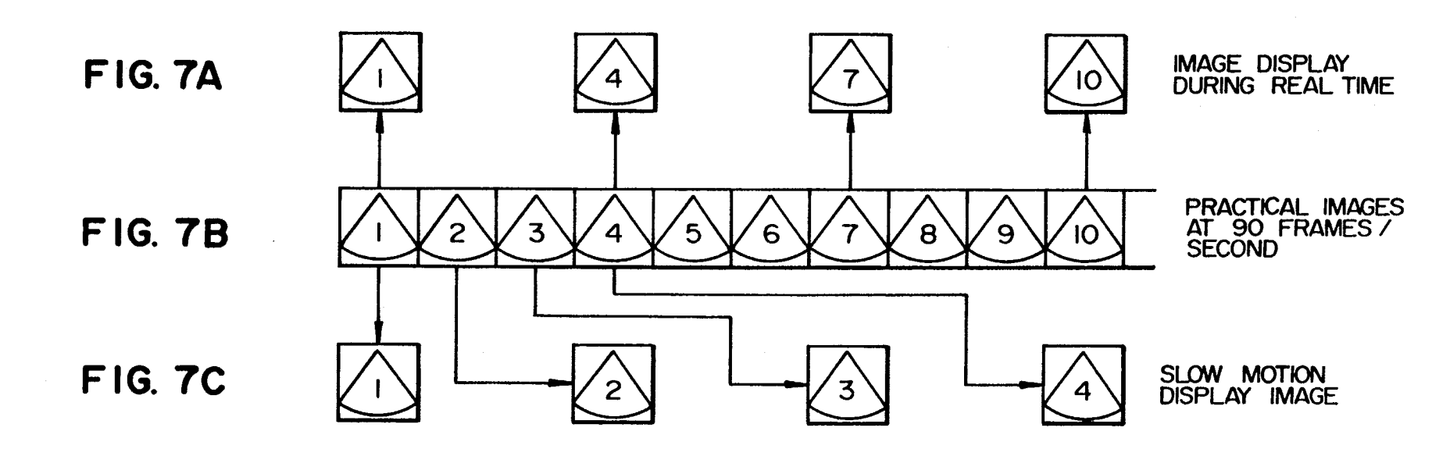
FIGS. 7A to 7C are diagrams for explaining states of image display obtained with the ultrasonic diagnosis apparatus shown in FIG. 5.

With this construction, when image data is readout of the image memory 5, suitable switching can be effected between delivery of image data at a rate of one out of n frame start signals F shown in FIG. 6B and delivery of image data in synchronism with the television vertical synchronizing signal V shown in FIG. 6E. This method is effective when the frame rate of image exceeds 30 frames/second. For example, when the sweep rate of display system is 30 frames/second for the frame rate of image being 90 frames/second in the conventional apparatus, only one out of three images at 90 frames/second is allowed to be displayed on the image display 8 during real time as shown in FIGS. 7A and 7B. Accordingly, in order to observe all of the images shown in FIG. 7B, it is inevitable to adopt a method wherein all images of 90 frames are once recorded in the image memory 5 shown in FIG. 3 and after being frozen, are delivered sequentially image by image from the image memory 5 to D/A converter 7 to permit display of all of the images.

Contrary to this, when in the embodiment shown in FIG. 5 the second frequency division signal A2 delivered out of the second frequency divider circuit 14' is selected, image data can be read in synchronism with the television vertical synchronizing signal V as shown in FIGS. 7B and 7B and images at 90 frames/second can be displayed in slow motion fashion at a rate of ⅓. At that time, given that one cardiac cycle is represented by 60/heart rate, the number N of observable frame images is so restricted as to be $$N \leq \text{one cardiac cycle} \times 30$$

but all images detected within a constant period T beginning with a desired timing can be observed during real time. In this case, T is subjected to a restriction condition indicated by the following equation:

$$T \leq \text{one cardiac cycle} \times 30/\text{frame rate}.$$

If all images at a high frame rate exceeding 30 frames/second are to be observed with the conventional apparatus, it is inevitable that all of the images be once stored in image storage means of large capacity and after being frozen, be reproduced image by image, and as a result an important phenomenon will possibly be missed during real time display; but according to the second embodiment shown in FIG. 5, all of the images can be displayed in slow motion fashion relative to a desired timing during real time and therefore, for example, a specific reaction of moving region which occurs only instantaneously can be observed on real time.

The FIG. 5 embodiment of the invention is not limitative and the read period of image data may be selected either to two or more integer times the write period or to one or more times the write period. In this case, the write period may be set to one or more integer times the period of the frame start signal F.

Figure 8:
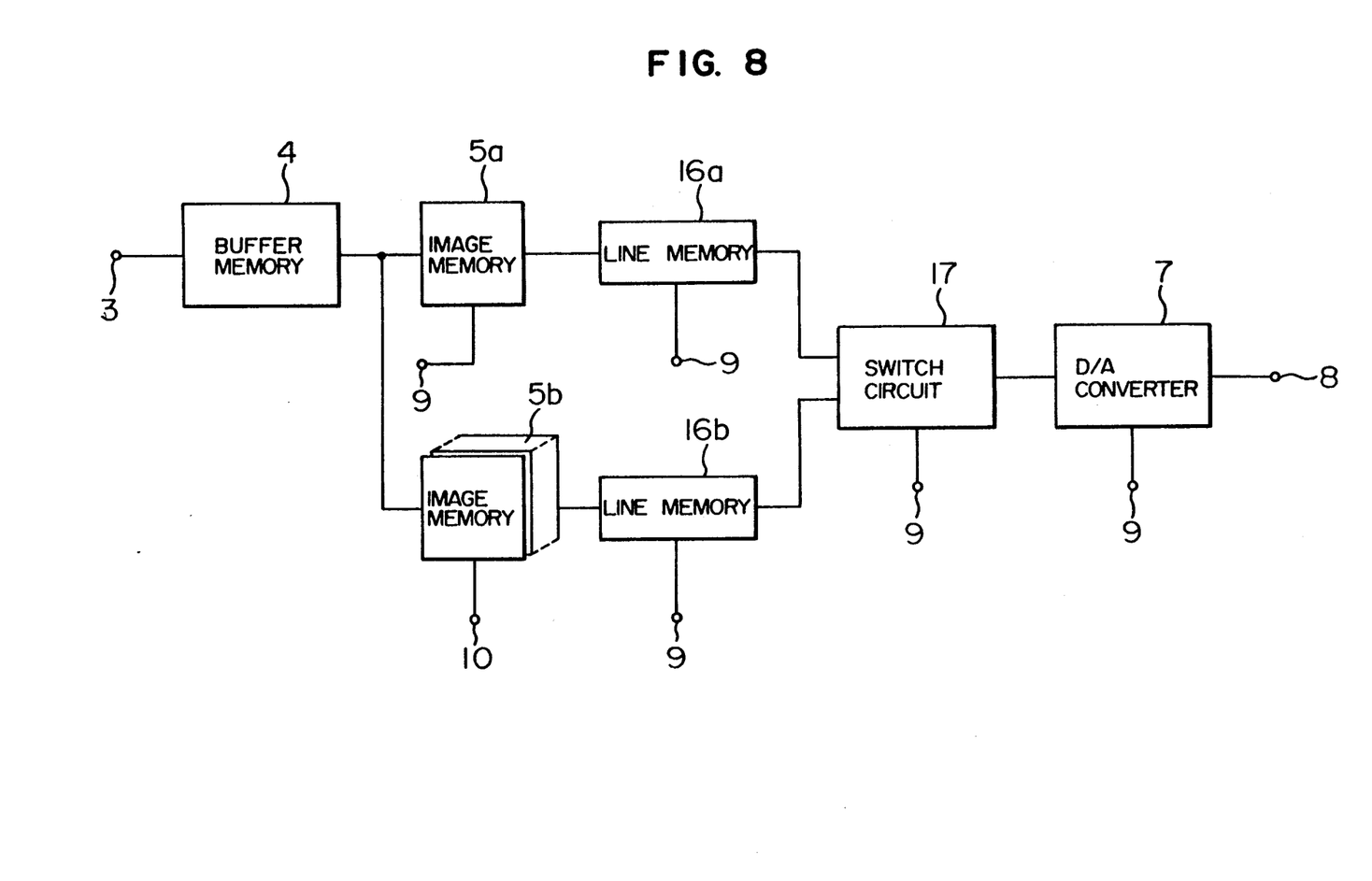
FIG. 8 is a block diagram showing the essential part of an ultrasonic diagnosis apparatus according to a further embodiment of the invention.

FIG. 8 is a block diagram showing the essential part of a further embodiment of the invention. In the present embodiment, in addition to a first image memory 5b corresponding to the image memory 5 succeeding the buffer memory 4 in the embodiments of FIGS. 1 and 5, a second image memory 5a is provided which stores original image data of real time display delivered out of the buffer memory 4. Further, in the present embodiment, first and second line memories 16a and 16b each corresponding to one horizontal scan of the image display 8 and respectively succeeding the image memories 5a and 5b are provided, and a switch circuit 17 for switching original image data from the first line memory 16a and slow motion image data from the second line memory 16b during horizontal scan of the image display 8.

Figure 9:
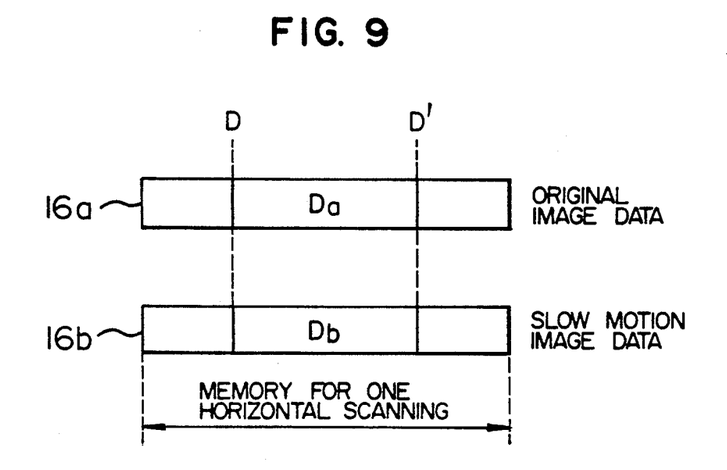
FIG. 9 is a timing chart for showing read operation of original image data and slow motion image data from line memories in the ultrasonic diagnosis apparatus shown in FIG. 8.

In operation, as shown in FIG. 9, original image data Da corresponding to one horizontal scan read out of the first image memory 5a is stored in the first line memory 16a and slow motion image data Db corresponding to one horizontal scan read out of the second image memory 5b is stored in the second line memory 16b. In order for the image data to be read out of the line memories 16a and 16b and displayed on the image display 8, the switch circuit 17 shown in FIG. 8 operates as shown in FIG. 9 in such a manner that image data covering an interval between a desired position D and a position D' distant from the position D by half of one horizontal scan is first delivered from the first line memory 16a storing the original image data Da and subsequently image data covering the same interval D-D' as above is delivered out of the second line memory 16b storing the slow motion image data Db.

Figure 10:
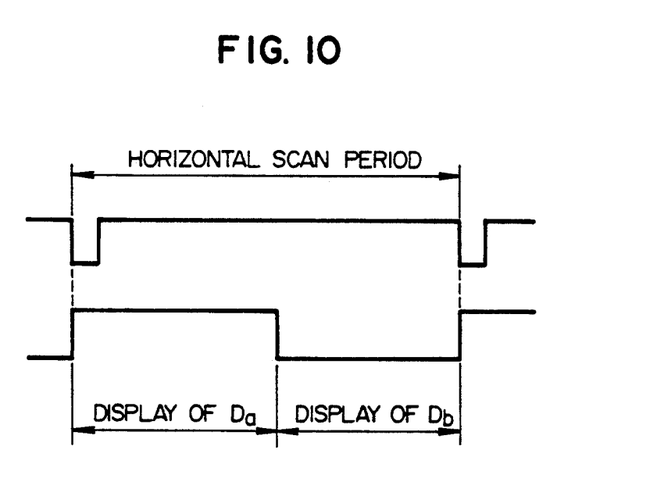
FIG. 10 is a timing chart showing states of control of display of image data on the image display in the ultrasonic diagnosis apparatus shown in FIG. 8.
Figure 11:
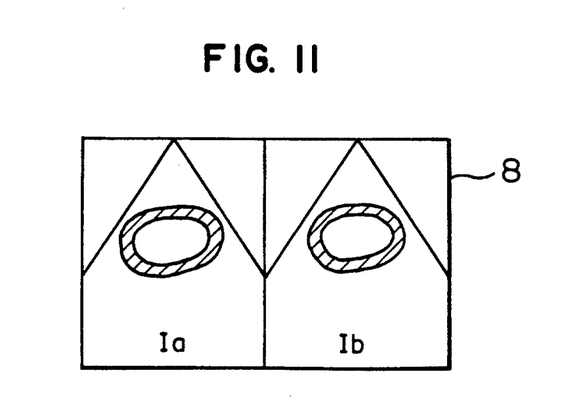
FIG. 11 is a diagram for explaining states of image display on the image display in the ultrasonic diagnosis apparatus shown in FIG. 8.

Thereafter, the original image data Da and slow motion image data Db are displayed on the image display 8 through the D/A converter 7 shown in FIG. 7 and at that time, the main controller 9 performs control such that the original image data Da is displayed during, for example, the first half of the horizontal scan period and the slow motion image data Db is displayed during the second half, as shown in FIG. 10. Consequently, as shown in FIG. 11, an original image Ia of real time display is displayed on one of, for example, right and left halves of the screen of the image display 8 and an image Ib of slow motion display during real time is displayed on the other in parallel.

Since in the embodiment shown in FIG. 8 the original image Ia of real time display and the image Ib of slow motion display during real time can be displayed in parallel on the same screen of the image display 8, the slow motion image Ib can be observed concurrently while observing the whole aspect of moving state of the internal organs through the original image Ia and more detailed diagnosis information about a region of interest can be obtained.

We claim:

1. An ultrasonic diagnosis apparatus comprising:
   ultrasonic wave transmitting/receiving means for transmitting ultrasonic signals to a subject and receiving reflected echo signals reflected from said subject;
   means for controlling said ultrasonic wave transmitting/receiving means such that the ultrasonic signals repetitively scan said subject at a predetermined scan period;
   image memory means for storing a plurality of image data pieces;
   detection means for detecting biophysical signals of said subject;
   means for setting a reference timing on a basis of the biophysical signals;
   image display means for displaying an image corresponding to said image data pieces being delivered out of said image memory means, said image display means displaying the image at a predetermined display period;
   means for controlling said image memory means so as to store said plurality of image data pieces based on the reflected echo signals, wherein said plurality of image data pieces respectively correspond to two-dimensional images of said subject at different time points and said time points associated with said plurality of image data pieces are sequentially displaced by a first time interval and in synchronism with said reference timing; and
   control means for controlling said image memory means so as to sequentially deliver said plurality of image data pieces stored in said image memory means at second time intervals longer than said first time interval during scanning of the ultrasonic signals.

2. An ultrasonic diagnosis apparatus according to claim 1 wherein said first time interval is N (N being an integer which is one or more) times said scan period.

3. An ultrasonic diagnosis apparatus according to claim 1 wherein an interval of said second time intervals is K (K being an integer which is one or more) times said display period.

4. An ultrasonic diagnosis apparatus according to claim 1 further comprising means for setting an interval of said second time intervals.

5. An ultrasonic diagnosis apparatus comprising:
   ultrasonic wave transmitting/receiving means for transmitting ultrasonic signals to a subject and receiving reflected echo signals reflected from said subject;
   means for controlling said ultrasonic wave transmitting/receiving means such that the ultrasonic signals repetitively scan said subject at a predetermined scan period;
   image memory means for storing a plurality of image data pieces;
   detection means for detecting biophysical signals of said subject;
   means for setting a reference timing on a basis of the biophysical signals;
   image display means for displaying an image corresponding to said image data pieces being delivered out of said image memory means, said image display means displaying the image at a predetermined display period;
   means for controlling said image memory means so as to store said plurality of image data pieces based on the reflected echo signals, wherein said plurality of image data pieces respectively correspond to two-dimensional images of said subject at different time points and said time points associated with said plurality of image data pieces are sequentially displaced by a first time interval and in synchronism with said reference timing; and
   control means for controlling said image memory means so as to sequentially deliver said plurality of image data pieces stored in said image memory means at second time intervals longer than said first time interval during scanning of the ultrasonic signals, wherein an interval of said second time intervals is M (M being an integer which is two or more) times said first time interval.

6. An ultrasonic diagnosis apparatus comprising:
   ultrasonic wave transmitting/receiving means for transmitting ultrasonic signals to a subject and receiving reflected echo signals reflected from said subject;
   means for controlling said ultrasonic wave transmitting/receiving means such that the ultrasonic signals repetitively scan said subject at a predetermined scan period;
   image memory means for storing a plurality of image data pieces;
   detection means for detecting biophysical signals of said subject;
   means for setting a reference timing on a basis of the biophysical signals;
   image display means for displaying an image corresponding to said image data pieces being delivered out of said image memory means, said image display means displaying the image at a predetermined display period;

means for controlling said image memory means so as to store said plurality of image data pieces based on the reflected echo signals, wherein said plurality of image data pieces respectively correspond to two-dimensional images of said subject at different time points and said time points associated with said plurality of image data pieces are sequentially displaced by a first time interval and in synchronism with said reference timing; and control means for controlling said image memory means so as to sequentially deliver said plurality of image data pieces stored in said image memory means at second time intervals longer than said first time interval during scanning of the ultrasonic signals, wherein said control means includes selector means for selecting one of said second time intervals which is M (M being an integer which is two or more) times said first time intervals and said second time interval which is K (K being an integer which is one or more) times said display period.

7. An ultrasonic diagnosis apparatus according to claim 6 wherein said first time interval is L (L being an integer which is one or more) times said scan period.

8. An ultrasonic diagnosis apparatus comprising:

ultrasonic wave transmitting/receiving means for transmitting ultrasonic signals to a subject and receiving reflected echo signals reflected from said subject;

means for controlling said ultrasonic wave transmitting/receiving means such that the ultrasonic signals repetitively scan said subject at a predetermined scan period;

first image memory means for storing a plurality of image data pieces;

second image memory means for storing a single image data piece;

detection means for detecting biophysical signals of said subject;

means for setting a reference timing on the basis of the biophysical signals;

image display means for displaying an image corresponding to an image data piece being inputted to said image display means, said image display means displaying the image at a predetermined display period;

means for controlling said first image memory means so as to store the plurality of image data pieces based on the reflected echo signals, wherein said plurality of image data pieces respectively correspond to two-dimensional images of said subject at different time points and said time points associated with said plurality of image data pieces are sequentially displaced by a first time interval and in synchronism with said reference timing;

means for sequentially overwriting respective image data pieces based on the reflected echo signals in said second memory means at third time intervals during scanning of the ultrasonic signals;

first control means for controlling said first image memory so as to sequentially deliver said plurality of data pieces stored in said first image memory means at second time intervals longer than said first time interval during scanning of the ultrasonic signals;

second control means for controlling said second memory means so as to sequentially deliver the image data pieces stored in said second image memory means; and display control means for displaying on said image display means both of an image corresponding to the image data piece being delivered out of said first memory means and an image corresponding to the image data piece being delivered out of said second memory means, on the basis of said image data piece being delivered out of said first memory means and said image data piece being delivered out of said second memory means.

9. An ultrasonic diagnosis apparatus according to claim 8 wherein said first time interval is N (N being an integer which is one or more) times said scan period.

10. An ultrasonic diagnosis apparatus according to claim 8 wherein an interval of said second time intervals is K (K being an integer which is one or more) times said display period.

11. An ultrasonic diagnosis apparatus according to claim 8 wherein an interval of said second time intervals is M (M being an integer which is two or more) times said first time interval.

12. An ultrasonic diagnosis apparatus according to claim 8 further comprising means for setting an interval of said second time intervals externally.

13. An ultrasonic diagnosis apparatus according to claim 8 wherein an interval of said third time intervals is P (P being an integer which is one or more) times said scan period.

14. An ultrasonic diagnosis apparatus according to claim 8 wherein said display control means includes:

first line memory means for sequentially storing respective partial data, corresponding to one horizontal scanning, included in said image data piece being delivered out of said first image memory means;

second line memory means for sequentially overwriting respective partial data, corresponding to one horizontal scanning, included in said image data piece being delivered out of said second image memory means; and means for alternately supplying to said image display means data, corresponding in amount to ½ horizontal scanning, included in the partial data stored in said first line memory means and data, corresponding in amount to ½ horizontal scanning, included in the partial data stored in said second line memory means.

* * * * *